United States Patent
Orton

(10) Patent No.: US 11,950,830 B2
(45) Date of Patent: Apr. 9, 2024

(54) ELECTRICAL FLUX DELIVERY AND RETURN CONFIGURATIONS FOR ELECTRICAL FLUX DELIVERY INSTRUMENTS, AND RELATED SYSTEMS AND METHODS

(71) Applicant: INTUITIVE SURGICAL OPERATIONS, INC., Sunnyvale, CA (US)

(72) Inventor: Michael Orton, Sunnyvale, CA (US)

(73) Assignee: Intutive Surgical Operations, Inc., Sunnyvale, CA (US)

( * ) Notice: Subject to any disclaimer, the term of this patent is extended or adjusted under 35 U.S.C. 154(b) by 766 days.

(21) Appl. No.: 16/315,434

(22) PCT Filed: May 15, 2017

(86) PCT No.: PCT/US2017/032688
§ 371 (c)(1),
(2) Date: Jan. 4, 2019

(87) PCT Pub. No.: WO2018/009274
PCT Pub. Date: Jan. 11, 2018

(65) Prior Publication Data
US 2019/0314079 A1    Oct. 17, 2019

Related U.S. Application Data

(60) Provisional application No. 62/359,512, filed on Jul. 7, 2016.

(51) Int. Cl.
*A61B 18/12*    (2006.01)
*A61B 18/00*    (2006.01)
(Continued)

(52) U.S. Cl.
CPC .......... *A61B 18/1206* (2013.01); *A61B 18/16* (2013.01); *A61B 34/37* (2016.02);
(Continued)

(58) Field of Classification Search
CPC ................ A61B 18/1206; A61B 18/16; A61B 2090/061; A61B 2018/00577;
(Continued)

(56) References Cited

U.S. PATENT DOCUMENTS 6,113,596 A * 9/2000 Hooven ................. A61B 18/14
606/42
8,423,182 B2 * 4/2013 Robinson ............... A61B 34/35
700/250
(Continued)

FOREIGN PATENT DOCUMENTS

CA       2297078 A1    1/1999
CN     102811677 A    12/2012
(Continued)

OTHER PUBLICATIONS

Mittelstein D., et al., "Novel Technique of a Multifunctional Electrosurgical System for Minimally Invasive Surgery," Journal of Neurosurgery, Apr. 29, 2016, vol. 126 (3), pp. 997-1002.
(Continued)

*Primary Examiner* — Joseph A Stoklosa
*Assistant Examiner* — Annie L Shoulders
(74) *Attorney, Agent, or Firm* — JONES ROBB, PLLC

(57) ABSTRACT

An electrosurgical flux supply unit includes a first terminal configured to deliver a first electrical flux, the first terminal being configured to be electrically coupled with a first electrode of a first electrosurgical instrument, a second terminal configured to receive a second electrical flux; the second terminal being configured to be electrically coupled with a second electrode of the first electrosurgical instru-
(Continued)

ment, and an electrical switching mechanism selectively configurable between a first state and a second state. In the first state, the electrical switching mechanism electrically couples the first electrode with the first terminal and, in the second state, the electrical switching mechanism electrically isolates the first electrode from the first terminal. The electrosurgical flux supply unit is configured to maintain the electrical coupling of the second terminal with the second electrode in both the first state and the second state of the electrical switching mechanism.

20 Claims, 7 Drawing Sheets

(51) Int. Cl.
*A61B 18/16* (2006.01)
*A61B 34/37* (2016.01)
*A61B 90/00* (2016.01)
(52) U.S. Cl.
CPC .............. *A61B 2018/00577* (2013.01); *A61B 2018/00827* (2013.01); *A61B 2018/00898* (2013.01); *A61B 2018/00958* (2013.01); *A61B 2018/1253* (2013.01); *A61B 2018/126* (2013.01); *A61B 2090/061* (2016.02)
(58) Field of Classification Search
CPC ........... A61B 2018/00827; A61B 2018/00898; A61B 2018/00958; A61B 2018/1253; A61B 2018/126
See application file for complete search history.

(56) References Cited

U.S. PATENT DOCUMENTS

| | | | | |
|---|---|---|---|---|
| 8,506,564 B2* | 8/2013 | Long | ................. | A61B 18/1477 606/41 |
| 8,506,864 B2* | 8/2013 | Tam | ..................... | B29C 48/405 264/211.21 |
| 9,314,620 B2* | 4/2016 | Long | ..................... | A61N 1/327 |
| 2004/0206365 A1* | 10/2004 | Knowlton | ............ | A61B 18/203 128/898 |
| 2005/0187539 A1* | 8/2005 | Takahashi | .......... | A61B 18/1402 606/1 |
| 2008/0039836 A1* | 2/2008 | Odom | ................ | A61B 18/1442 606/51 |
| 2008/0319436 A1* | 12/2008 | Daniel | ................. | A61B 18/148 606/41 |
| 2010/0152726 A1 | 6/2010 | Cadouri et al. | | |
| 2014/0128861 A1* | 5/2014 | Leung | ................. | A61B 18/148 606/33 |
| 2014/0142567 A1 | 5/2014 | Poulsen | | |
| 2015/0126998 A1* | 5/2015 | Batchelor | .......... | A61B 18/1445 606/42 |
| 2016/0074093 A1* | 3/2016 | Shimizu | ............. | A61B 18/1206 606/35 |
| 2018/0206905 A1* | 7/2018 | Batchelor | .............. | A61B 18/14 |

FOREIGN PATENT DOCUMENTS

| | | |
|---|---|---|
| CN | 103596514 A | 2/2014 |
| CN | 103764057 A | 4/2014 |
| CN | 105142557 A | 12/2015 |
| CN | 105744908 A | 7/2016 |
| WO | WO-2004078051 A2 | 9/2004 |
| WO | WO-2014071184 A1 | 5/2014 |
| WO | WO-2014145148 A2 | 9/2014 |

OTHER PUBLICATIONS

International Search Report and Written Opinion for Application No. PCT/US2017/032688, dated Aug. 22, 2017, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action dated Jan. 8, 2021 for Chinese Application No. 201780049476 filed May 15, 2017, 21 pages.
Office Action dated Feb. 28, 2022 for Chinese Application No. 201780049476 filed May 15, 2017, 22 pages.

* cited by examiner

ELECTRICAL FLUX DELIVERY AND RETURN CONFIGURATIONS FOR ELECTRICAL FLUX DELIVERY INSTRUMENTS, AND RELATED SYSTEMS AND METHODS

CROSS-REFERENCE TO RELATED APPLICATION

This application is a U.S. national stage application under 35 U.S.C. § 371(c) of International Application No. PCT/US2017/032688, filed on May 15, 2017, which claims priority to U.S. Provisional Patent Application 62/359,512, filed on Jul. 7, 2016, the entire content each of which is incorporated by reference herein in its entirety.

TECHNICAL FIELD

Aspects of the present disclosure relate to electrical flux delivery instruments and related systems and methods, such as, for example, electrosurgical instruments, systems, and methods for delivering electrical flux energy to perform electrosurgical procedures.

INTRODUCTION

Remotely controlled surgical instruments, including both manual, laparoscopic instruments and computer-assisted, teleoperated surgical instruments (sometimes referred to as robotic surgical instruments), are often used in minimally invasive medical procedures. For example, in teleoperated surgical systems, surgeons manipulate input devices at a surgeon console, and those "master" inputs are passed to a patient side cart that interfaces with one or more remotely controlled surgical instruments coupled to the patient side cart. Based on the surgeon inputs at the surgeon console, the one or more remotely controlled surgical instruments are actuated at the patient side cart to operate on the patient, thereby creating a master-slave control relationship between the surgeon console and the surgical instrument(s) at the patient side cart.

Some surgical instruments, such as electrosurgical instruments and other types of surgical instruments, comprise end effectors that are configured to deliver a flux (e.g., electrical energy, thermal energy, ultrasonic energy, irrigation, suction, etc.) to material such as tissue, or a tissue-like material for testing purposes. Such surgical instruments are coupled to a flux supply unit, such as electrosurgical energy generating units (ESU's) in the case of an electrosurgical instrument. For instance, an ESU may generate and supply electrical flux energy to an end effector of an electrosurgical instrument, so that an electrosurgical energy can be applied to tissue at or near the end effector.

Different end effectors are used to perform surgical procedures on tissue, using either monopolar or bipolar flux energy, depending on the type of instrument or procedure. Monopolar electrosurgery can be used for several procedures, including cut, blend, desiccation, and fulguration. Generally, with monopolar electrosurgery, the flux is delivered to the material (for example, tissue) via a single "active" electrode of an end effector, and returned to the ESU via a return electrode of a return or "ground" pad, thereby completing an electrical circuit. For example, an end effector of a monopolar instrument comprising a single electrode can be placed in an entry site of a patient and used to perform surgical procedures such as those described herein. During the procedure, the return pad is attached to the patient's body, such as at a thigh and/or back, for example, so that any residual or excess electrical flux energy (i.e., energy that was not converted to another form of energy such as heat) flows from the generator to the electrode, through the target tissue to the return pad, and back to the generator.

Return pads are subject to poor electrical flow, particularly since they are not under the direct control of the surgeon operating the instruments. For example, the surgeon is typically unable to observe and directly control the position of the return pad during the procedure. To compensate for poor electrical flow, a higher amount of energy may be employed to operate the electrical flux delivery of the instrument. This may in turn limit fine control of the instrument, and may subject the system to capacitive coupling, for example, in the tubes and cables leading back to the ESU and/or to other parts of the instrument itself. In contrast to monopolar instruments, bipolar electrosurgical instruments deliver electrical energy flux through the tissue using an end effector comprising at least two electrodes, thereby using less energy. However, in light of their lower energy configuration, bipolar electrosurgical instruments are generally less effective at cutting and coagulating large bleeding areas, particularly when the material being operated upon cannot be effectively contacted on both sides by the two electrodes. Consequently, some electrosurgical procedures, such as, for example, spray, blend, and/or fulguration procedures, are difficult to perform using a bipolar instrument.

Thus, it is desirable to continue to improve upon electrical flux delivery and return instruments, methods, and systems to address the above and other unresolved issues of conventional instruments, systems, and methods.

SUMMARY

Exemplary embodiments of the present disclosure may solve one or more of the above-mentioned technical challenges and/or may demonstrate one or more of the above-mentioned desirable features. Other features and/or advantages may become apparent from the description that follows.

In accordance with at least one exemplary embodiment, the present disclosure contemplates an electrosurgical flux supply unit including a first terminal configured to deliver a first electrical flux, the first terminal being configured to be electrically coupled with a first electrode of a first electrosurgical instrument operably coupled to the electrosurgical flux supply unit, a second terminal configured to receive a second electrical flux, the second terminal being configured to be electrically coupled with a second electrode of the first electrosurgical instrument. The electrosurgical flux supply unit also comprises an electrical switching mechanism selectively configurable between a first state and a second state. In the first state, the electrical switching mechanism electrically couples the first electrode with the first terminal and, in the second state, the electrical switching mechanism electrically isolates the first electrode from the first terminal. The electrosurgical flux supply unit is configured to maintain the electrical coupling of the second terminal with the second electrode in both the first state and the second state of the electrical switching mechanism.

In accordance with another exemplary embodiment, the present disclosure contemplates an electrosurgical system comprising an electrosurgical flux supply unit, a first electrosurgical instrument electrically coupled to the electrosurgical flux supply unit, and a second electrosurgical instrument electrically coupled to the electrosurgical flux supply unit. The electrosurgical flux supply unit is configured to set a first electrode of a first end effector of the first electrosurgical instrument at a first electrical potential, set a second electrode of a second end effector of the second electrosurgical instrument at a second electrical potential, the second electrical potential being at a relative ground to the first electrical potential, deliver an electrical flux to the first electrode, and receive, from the second electrode, a portion of the electrical flux delivered to the first electrode.

In accordance with another exemplary embodiment, the present disclosure contemplates a method for performing electrosurgery, including setting a first electrode of a first end effector of a first electrosurgical instrument at a first electrical potential, setting a second electrode of a second end effector of a second electrosurgical instrument at a second electrical potential, the second electrical potential being set at a relative ground to the first electrical potential, delivering an electrical flux to the first electrode, and receiving, at a ground terminal electrically coupled to the second electrode, a portion of the delivered electrical flux.

In accordance with another exemplary embodiment, the present disclosure contemplates a method comprising receiving, from an electrosurgical flux supply unit, a first electrical flux at a first electrode of a first end effector of a first electrosurgical instrument. The method further comprises applying, by the first electrode, the first electrical flux to a target material, wherein application of the first electrical flux to the target material results in a second electrical flux through the target material. The method also comprises transmitting, to the electrosurgical flux supply unit, the second electrical flux from a second electrode of a second end effector of a second electrosurgical instrument, with the second end effector of the second electrosurgical instrument positioned proximate the target material.

In accordance with another exemplary embodiment, the present disclosure contemplates an electrosurgical system comprising a first electrosurgical instrument configured to receive an electrical flux energy from an electrosurgical flux supply unit at a first electrode set at a first electrical potential, and a second electrosurgical instrument configured to return a portion of the electrical flux energy to the electrosurgical flux supply unit from a second electrode set at a second electrical potential. The second electrical potential is at relative ground to the first electrical potential.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
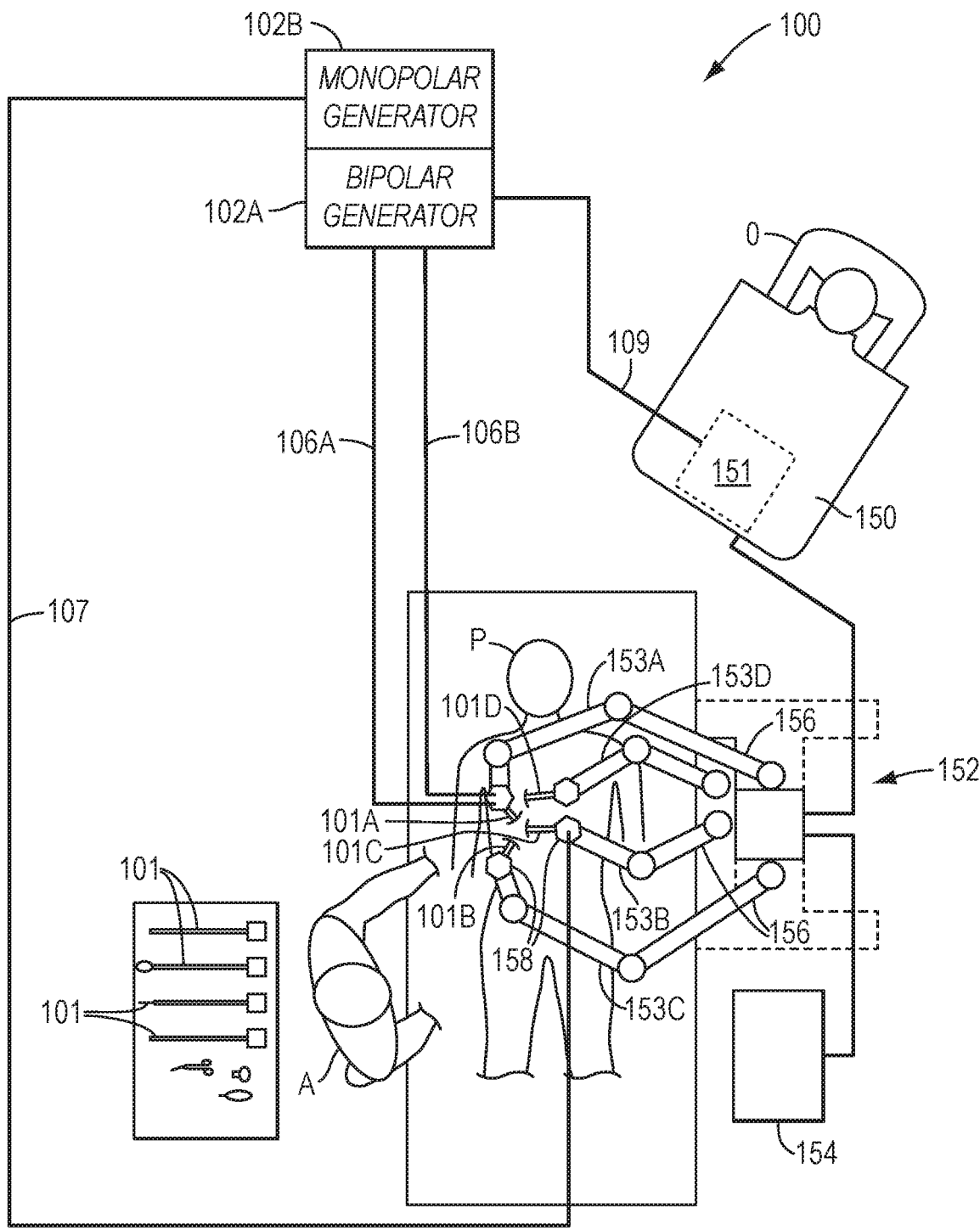
FIG. 1 is diagrammatic view of an exemplary embodiment of a teleoperated surgical system.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates various configurations for delivering and returning electrical flux energy between a generator (e.g. an ESU) and one or more electrosurgical instruments. The electrical flux return configurations and techniques according to exemplary embodiments of the present disclosure may facilitate the surgical procedure by providing the surgeon with a clear indication of and control over the electrical flux return state; for example, return pads placed in contact with a patient may be reduced or may no longer be needed. Further, a reduction in energy supply to an electrosurgical instrument may be realized using various exemplary embodiments of the present disclosure. For the purposes of the present disclosure, the terms "electrical flux energy", "flux energy", "electrical energy", "electrical energy flux", and so on are synonymous, and generally representing the flow of electrical energy through components of the disclosed devices and systems. The electrical energy may be, for example, electrical current with a flow generated by setting terminals of a supply unit (and electrodes connected thereto) to specific voltages or electrical potentials.

The present disclosure contemplates the use of an electrosurgical instrument as an electrical flux delivery return for another electrosurgical instrument. For example, a return electrode of a bipolar instrument in the proximity of the monopolar instrument (inside the patient) can be configured as a return electrode for a monopolar instrument. Flux energy in the form of electrical current is delivered or via an electrode of the monopolar instrument and returned via the return electrode of the bipolar instrument. When the monopolar instrument is in use to perform an electrosurgical procedure, the bipolar instrument in the proximity of the monopolar instrument is kept in contact with the patient's body, thereby reducing or eliminating the need to affix a return pad to the patient's body. In further exemplary embodiments, exemplary ESUs are configured with appropriate mechanisms for switching the functionality of the bipolar instrument from a bipolar mode to a return mode. In other exemplary embodiments, two bipolar instruments may be used together with one being configured to deliver energy as a monopolar instrument, such that flux energy is delivered via an active electrode of the one bipolar instrument, and the other is configured for use as an electrical flux return such that the electrical flux is returned via one of the electrodes (the "return" electrode) of the other bipolar instrument. Configuring a bipolar instrument as a return for electrical flux energy can provide the ability for the surgeon to have full control over the location and motion of the return electrode within the bipolar instrument. This control enables the surgeon operating the monopolar instrument to add traction and counter traction on the tissue being operated upon with the bipolar instrument configured as an energy return. Further, using the bipolar instrument as an energy return minimizes the distance between the active electrode (of the monopolar instrument) and the return electrode (of the bipolar instrument), thereby minimizing the resistance encountered by the flux energy passing through the tissue, consequently using less energy than traditional monopolar operation.

For ease of description, various exemplary embodiments set forth below describe electrosurgical instruments that are remotely controlled (e.g., via teleoperation or manually) by a surgeon, and powered by energy supply sources or generators that deliver an electrical flux, such as electrical energy for cautery procedures, which may, for example, range from 100s of volts to 1000s of volts.

Non-limiting, exemplary embodiments of teleoperated surgical systems with which the principles of the present disclosure may be utilized include the da Vinci® Si (model no. IS3000) da Vinci® Si Surgical System, Single Site da Vinci® Surgical System, or a da Vinci® Xi Surgical System, available from Intuitive Surgical, Inc. of Sunnyvale, California. However, persons having ordinary skill in the art will appreciate that the present disclosure can be applied to a variety of surgical systems including automated or manual (hand-held) laparoscopic surgical systems that utilize electrosurgical instruments and electrosurgical energy generation units (ESUs) to perform electrosurgical procedures.

FIG. 1 depicts a diagrammatic view of an exemplary teleoperated surgical system 100 for performing minimally invasive surgical procedures using a number of remotely controlled (robotic) instruments. Two electrosurgical instruments, electrosurgical instrument 101A and electrosurgical instrument 101B are depicted in use in FIG. 1. FIG. 1 also depicts an imaging instrument, an endoscopic camera 101C, in use. Each of the electrosurgical instruments 101A and 101B are robotic surgical instruments that are manipulated by a slaved robotic manipulator system 152 (sometimes referred to as a patient side cart) 152 and remotely controlled by control signals received from a master control console 150. In the exemplary embodiment of FIG. 1, electrosurgical instrument 101A is a bipolar electrosurgical instrument and electrosurgical instrument 101B is a monopolar electrosurgical instrument. A user or operator O (generally a surgeon) performs a minimally invasive surgical procedure on patient P by manipulating input devices at master control console 150. Master control console 150 may also be referred to herein as a control console, a surgeon console, a master console, or a console. A computer system 151 of console 150 directs movement of the instruments 101A, 101B, 101C (which as explained below may be an endoscopic imaging device), effecting movement of the instruments using robotic surgical manipulator system 152. For example, foot pedals and master controllers of console 150 provide integrated control mechanisms that a surgeon may use to control every aspect of the surgical system to make surgery more efficient. Advanced user interfaces may be used to provide improved control and feedback of operating the remote controllable equipment with the surgical instruments.

Surgical manipulator system 152 may also be referred to as patient-side cart system or as a cart. The surgical manipulator system 152 has one or more jointed manipulator arms 153 to support the surgical instruments, including generally an image capture device. For example, the surgical manipulator system 152 includes four manipulator arms 153 supported by jointed linkages, with a central arm configured to support an endoscopic camera 101C and the surgical arms 153A, 153B, 153D to left and right of center supporting tissue manipulation instruments (cannulas) and surgical instruments 101A, 101B, 101D. An assistant A may assist in pre-positioning of the surgical manipulator system 152 (sometimes called "patient side cart 152" when configured to be used beside the patient at least some of the time during operation) and its arms relative to patient P as well as swapping tools or instruments 101 for alternative instrument structures, and the like, while viewing the internal surgical site via an assistant's display 154 that can be located on an auxiliary cart or other centrally accessible portion of the surgical system.

To support the functionality of the electrosurgical instruments 101A, 101B, the surgical system 100 may further include one or more electrosurgical generators 102A, 102B. The one or more electrosurgical generators 102A, 102B typically supply high voltage, low current electrical energy of various wave forms to instruments 101A, 101B for performing procedures such as, for example, cautery, cutting tissue, or sealing a vessel, and are remotely controlled by the master control console 150 over a control cable 109 by a surgeon O operating the master console. The electrosurgical generator 102A is a bipolar generator, and the electrosurgical generator 102B is a monopolar generator. Electrosurgical generators 102A, 102B may be combined together into one electrosurgical unit (ESU) that is remotely controlled by two sets of controls from the master control console 150, and the ESU may include any number of ports designed to provide differing numbers of bipolar and/or monopolar energy to surgical instruments. The ESU may be mounted on a control cart (not shown), for example, with the display 154, that includes a computer and an optional interface. The computer may be communicatively coupled to computer system 151. Either computer may include one or microprocessors to execute instructions and storage devices to store software with executable instructions that may be used to generate control signals to control the surgical system 100. Either computer may further include a sound generator and one or more speakers to generate audible sounds, a haptic/tactile feedback generator and one or more vibrating devices to generate vibrations, and a graphics controller/generator to generate a graphical user interface (GUI). In exemplary embodiments, the ESU may comprise components similar or identical to the ForceTriad™ FT-10 by COVIDIEN™, ENSEAL™ system by ETHICON™, or GYRUS™ G400 by OLYMPUS™.

A pair of wires 106A-106B electrically couple the bipolar electrosurgical generator 102A and the bipolar electrosurgical instrument 101A. The pair of wires 106A, 106B may transfer the energy of the bipolar electrosurgical generator 102A to a respective pair of electrodes of the end effector of the bipolar electrosurgical instrument 101A to perform electrosurgical procedures. Similarly, a wire 107 electrically couples the monopolar electrosurgical generator 102B and the monopolar electrosurgical instrument 101B. The wire 107 may transfer the energy of the monopolar electrosurgical generator 102B to an electrode of an end effector of the monopolar electrosurgical robotic instrument 101B to perform electrosurgical procedures. As explained above, generally a ground or return wire (not shown) is coupled between the monopolar electrosurgical generator 102B and a return pad (not shown) attached to patient P, the exemplary embodiments described herein are configured to utilize one of the pair of wires 106A, 106B as a return wire, for example, in lieu of utilizing a return pad. Moreover, one or more of electrosurgical generators 102A, 102B and computer system 151 can be configured to determine what type of flux energy and levels thereof that the electrosurgical instruments 101A, 101B may receive, and to switch between a bipolar mode, a monopolar mode, and an energy return mode as further described herein.

Figure 2A:
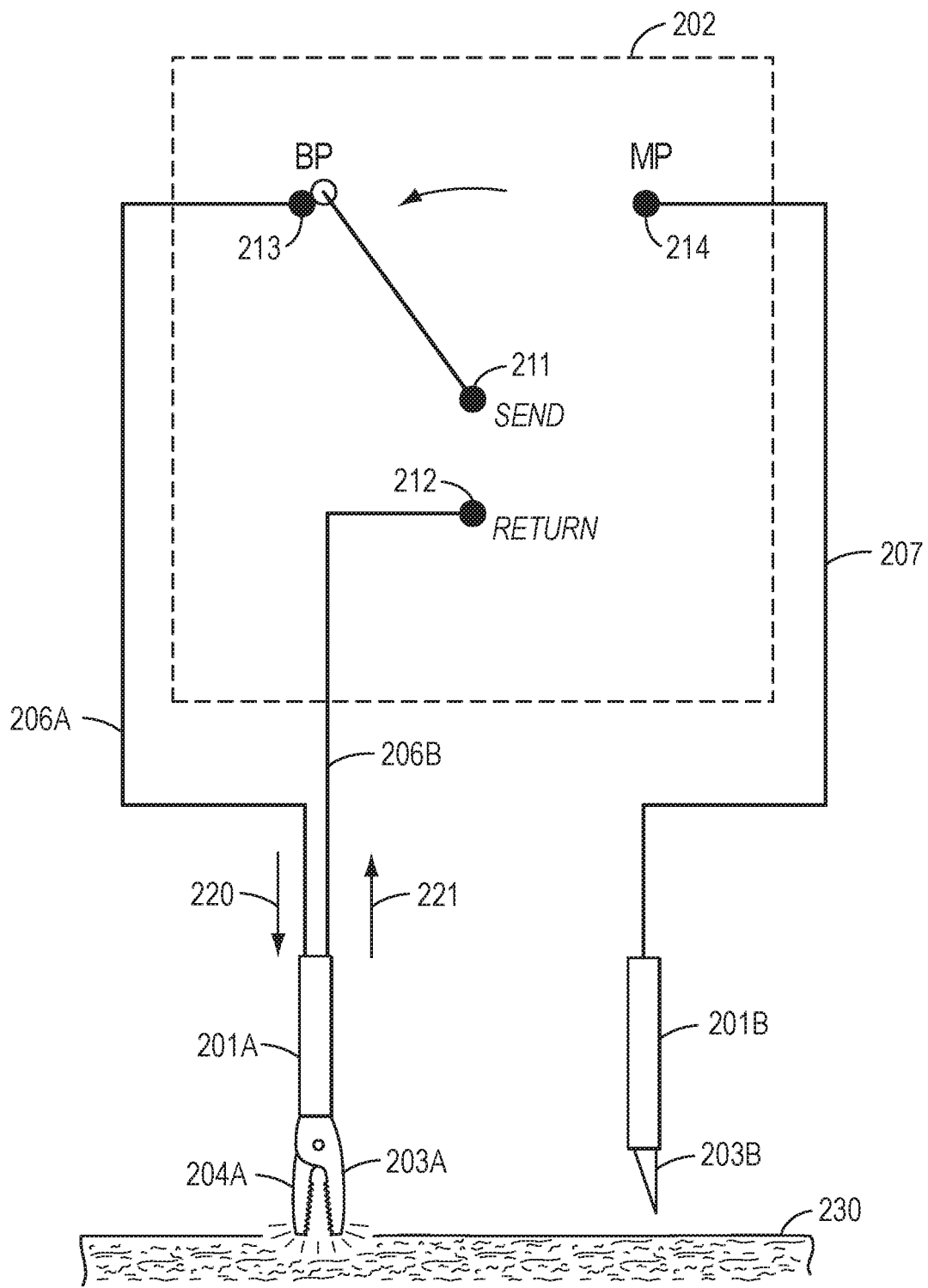
FIGS. 2A-2B are schematic views of an exemplary embodiment of an electrosurgical supply unit (ESU) operating in a bipolar mode and in a monopolar mode with an electrical energy flux return, respectively.
Figure 2B:
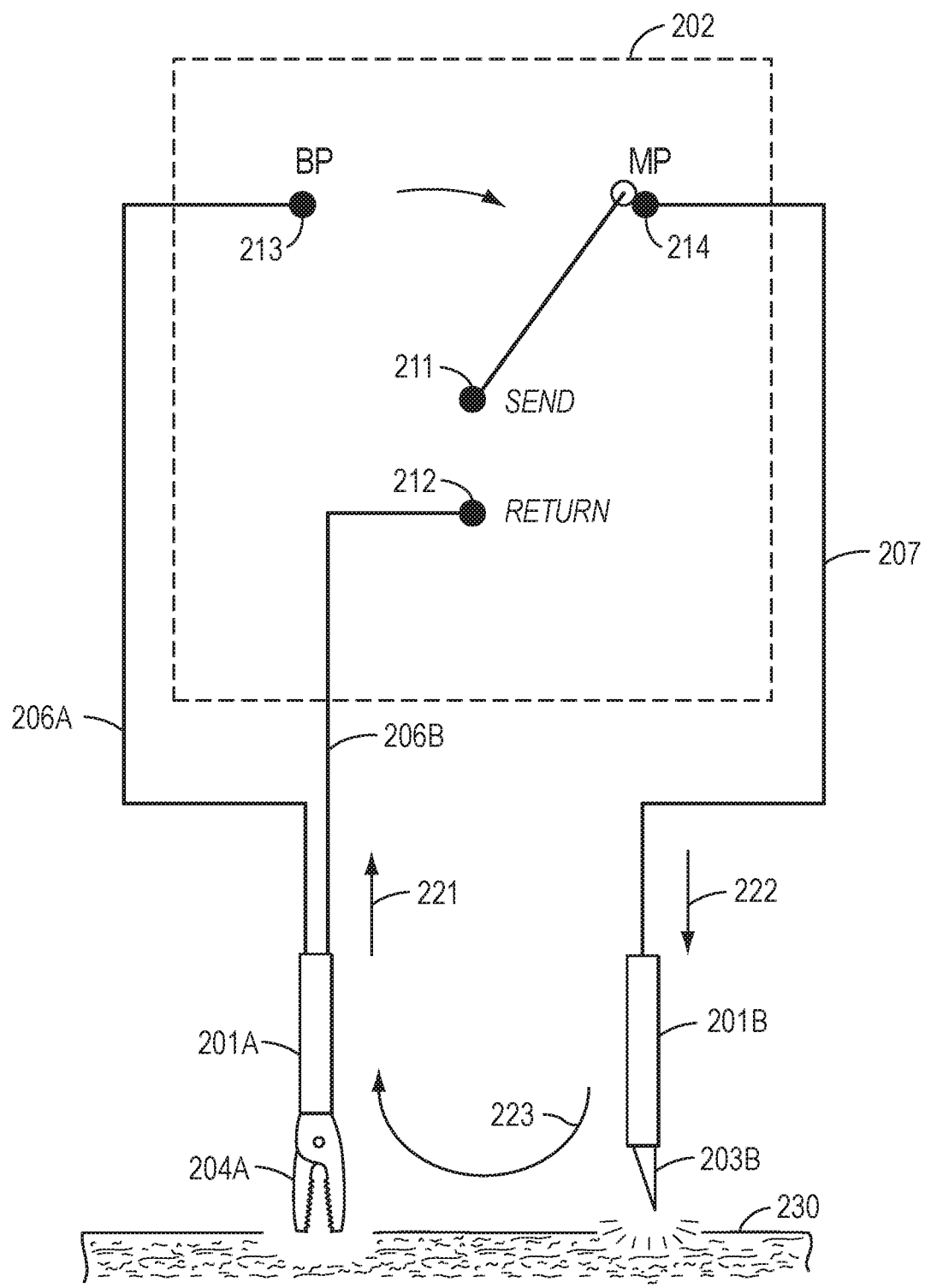

FIGS. 2A-2B show schematic illustrations of an exemplary embodiment of an electrosurgical supply unit (ESU) 202 coupled with electrosurgical instruments 201A, 201B and respectively operating in a bipolar mode (FIG. 2A), and a monopolar mode with a bipolar instrument energy return (FIG. 2B) in accordance with the present disclosure. Although only two instruments 201A and 201B are shown, any number of electrosurgical instruments can be powered by ESU 202, and various types of instruments may be used besides the instruments shown. ESU 202 comprises a source terminal 211 for delivering flux energy, such as electrical current, to an electrode of an electrosurgical instrument, and a return terminal 212 for providing a return or "ground" to another electrode. The flux energy may be delivered by setting a source terminal at a first potential or voltage (with a polarity set to either positive or negative), and the return terminal to a second potential at a relative ground to the first electrical potential, such that a circuit is formed between the two terminals during operation of electrosurgical instruments connected thereto. Although terminals 211 and 212 are described for convenience as "source" and "return", in practice the functions of each terminal 211, 212 are interchangeable, and the polarities may be switched, particularly when the type of signal being transmitted to an instrument is an alternating current (AC) signal. Moreover, for the purposes of the subject disclosure, the term "ground" or "relative ground" may be an actual earth potential, or any potential that is isolated from the circuit. In either case, it will be noted that source terminal 211 is configured as a switch between a bipolar port 213 and a monopolar port 214, while return terminal 212 is configured as a return from bipolar instrument 201A only. Electrosurgical instruments 201A, 201B are operated by a surgeon, either directly or via a remote interface, to perform electrosurgical procedures on a material 230, such as tissue for example. (Thus, "material 230" may be referred to as "tissue 230" in this disclosure.) Tissue 230 can be any type of tissue, such as neural tissue, muscle tissue, vascular tissue, etc.

In operation, with reference to FIG. 2A, source terminal 211 is set to a bipolar mode, i.e. connected to bipolar port 213. Thus, flux energy flows from bipolar port 213, through wire 206A, and to a first, active electrode 203A of electrosurgical instrument 201A comprising an end effector with two electrodes 203A, 204A that are configured to be independently operated. The flux energy flows in a direction depicted by arrow 220. Electrosurgical instrument 201A may be, for instance, a vessel sealer, forceps, or any instrument that has an end effector comprising two electrodes. For example, electrosurgical instrument 201A can comprise components similar or identical to the LIGASURE™ by COVIDIEN™ or the THUNDERBEAT™ by OLYMPUS™. As described above with reference to a conventional operation of a bipolar electrosurgical instrument, any flux energy remaining after flowing through tissue 230 is returned to a second, return electrode 204A of the end effector of the electrosurgical instrument 201A. This return flux energy flows from second, return electrode 204A, through return wire 206B, along direction indicated by arrow 221, and back to return terminal 212 of ESU 202. Moreover, although source terminal 211 is depicted as being connected only to bipolar port 213 and not to monopolar port 214, this is merely a convenient depiction intended to convey the bipolar mode of operation, and other switching mechanisms that enable simultaneous use of instruments 201A, 201B may be appreciated by those having ordinary skill in the art in light of the present disclosure.

With reference now to FIG. 2B, source terminal 211 is switched over to deliver flux energy via monopolar port 214, through wire 207, and to an active electrode 203B of an end effector of monopolar instrument 201B, in a direction indicated by arrow 222. Electrosurgical instrument 201B may comprise any monopolar instrument, for instance, an instrument having an end effector comprising a single electrode for delivery of electrical flux, and being configured to perform various electrosurgical procedures, such as for example spray, fulguration, cutting, coagulation, desiccation, or sealing of tissue 230. As depicted in FIG. 2B, in this mode of operation, return terminal 212 of ESU 202 remains electrically coupled with the second, return electrode 204A of bipolar electrosurgical instrument 201A, such that bipolar electrosurgical instrument 201A can continue to be operated as an electrical flux energy return. To perform the function of a return electrode for monopolar instrument 201B, at least the return electrode 204A of bipolar electrosurgical instrument 201A is maintained in physical contact with the tissue 230. Consequently, any excess flux energy flowing through tissue 230 is returned along direction indicated by arrow 223, through return electrode 204A of electrosurgical instrument 201A, through return wire 206B along a direction indicated by arrow 221, and back to return terminal 212.

The depicted configuration may thus be referred to as a monopolar mode using a bipolar instrument as an energy return. In other words, monopolar instrument 201B is the primary instrument being operated, and bipolar instrument 201A is used as an energy return, thereby reducing or eliminating the need for a return pad attached elsewhere on tissue 230. In this way, the surgeon operating instruments 201A, 201B is able to exercise full control over the location and motion of the return electrode of bipolar instrument 201A, thereby being able to provide traction and counter traction on tissue 230 using both instruments simultaneously. For example, the surgeon can apply tension to tissue 230 using at least one instrument with one hand while applying tension using another instrument with the other hand. Moreover, the distance between active electrode 203B of monopolar instrument 201B and the return electrode 204A of bipolar instrument 201A is relatively small compared to a distance when using a return pad attached elsewhere on the patient (i.e. not in the proximity of tissue 230). Thus, less energy may be used when performing the same monopolar procedure by using monopolar instrument 201B with the bipolar instrument 201A as an energy flux return, than in a traditional monopolar operation that uses a return or ground pad. This is due to the resulting reduction in distance (and therefore the resistance) between the active electrode 203B of the monopolar instrument 201B and the return electrode 204A of the bipolar instrument 201A.

In various exemplary embodiments, return electrode 204A of bipolar instrument 201A has a larger surface area relative to the active electrode 203B of monopolar instrument 201B. Such an increase in the ratio of surface area helps to minimize arcing between monopolar instrument 201B and tissue 230 that is often caused by the higher energy required for traditional monopolar operation using a return pad for electrical flux energy return. In an exemplary embodiment, the surface area of the return electrode of an end effector of a bipolar instrument is at least three times larger than the surface area of an electrode of the end effector of a monopolar instrument.

Figure 3A:
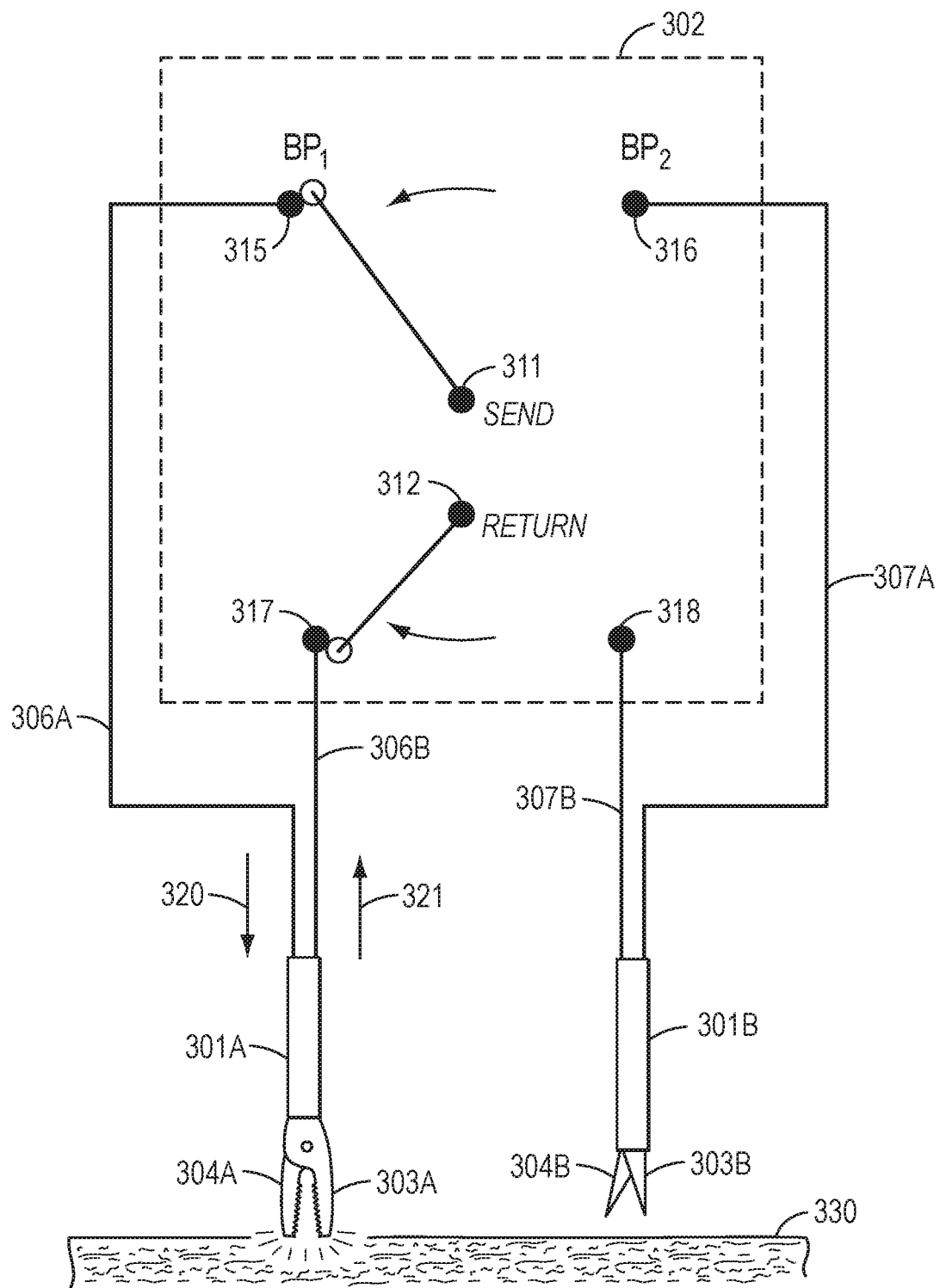
FIGS. 3A-3C are schematic views of an exemplary embodiment of an ESU operating in a first bipolar mode, in a second bipolar mode, and in a monopolar mode with an electrical energy return, respectively.
Figure 3B:
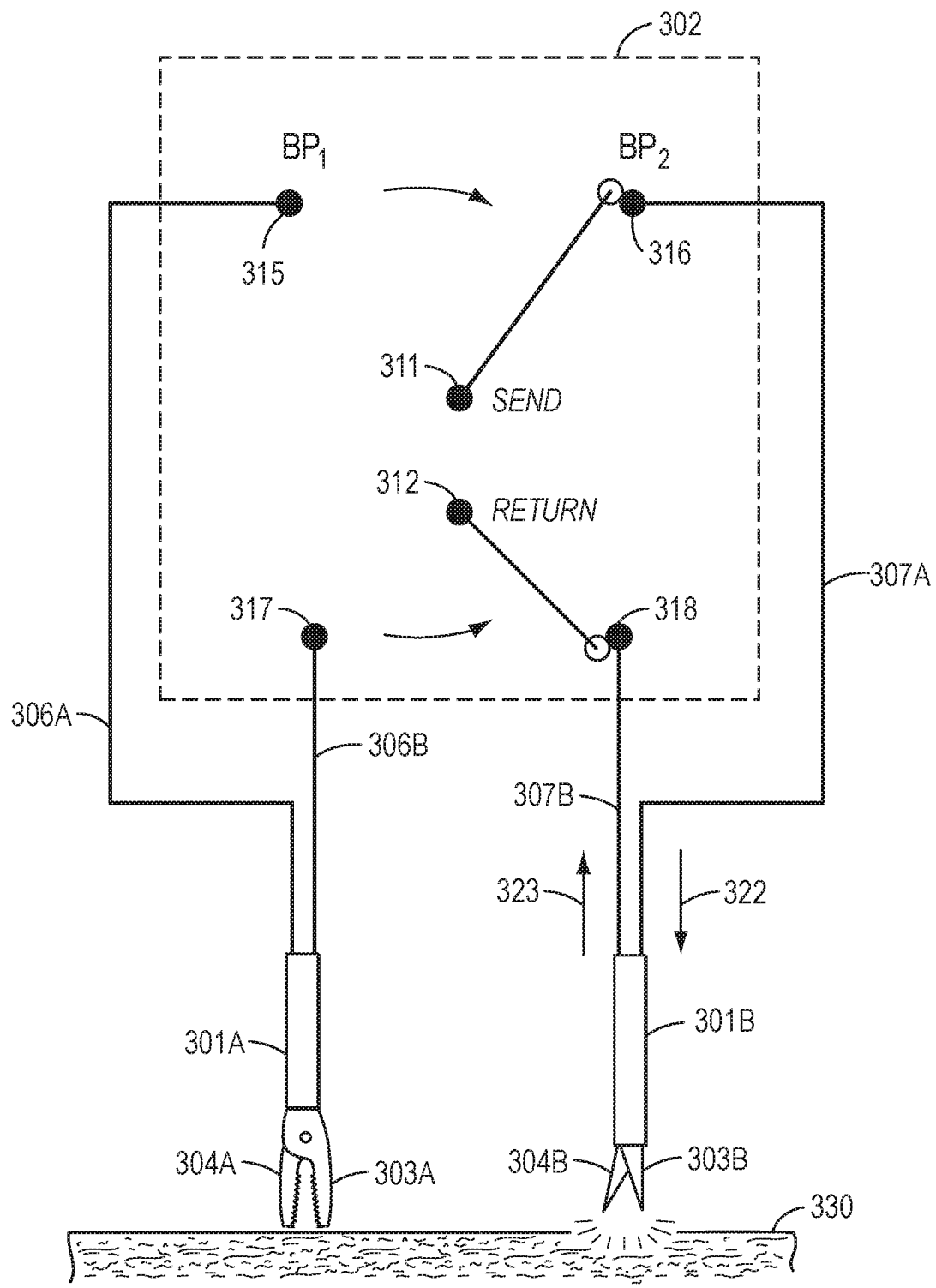
Figure 3C:
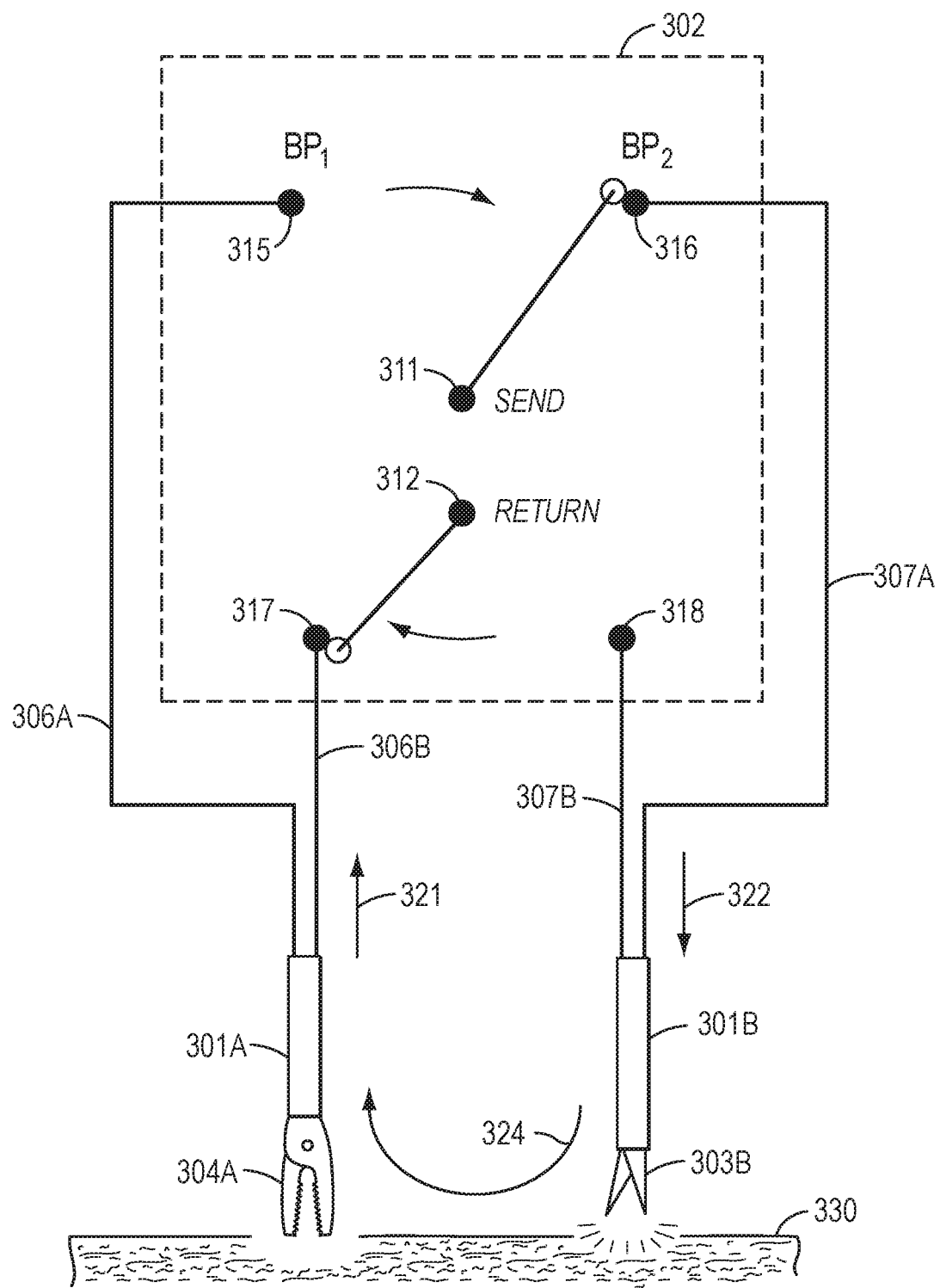

FIGS. 3A-3C show schematic illustrations of an exemplary embodiment of an ESU 302 coupled with a bipolar electrosurgical instrument 301A and a monopolar electrosurgical instrument 301B and operating in first and second bipolar modes (FIGS. 3A-3B, respectively) and a monopolar mode with an bipolar instrument energy return (FIG. 3C) in accordance with the present disclosure. Although only two instruments 301A and 301B are shown, any number of electrosurgical instruments can be powered by ESU 202, and various types of instruments may be used to perform operations illustrated herein. Similar to the ESU 202 in FIGS. 2A-2B, ESU 302 comprises a source terminal 311 for delivering electrical flux energy to an electrode of an electrosurgical instrument, and a return terminal 312 for providing a return or "ground" to another electrode. The flux energy may be delivered by setting a source terminal to a first potential or voltage (with a polarity set to either positive or negative), and the return terminal to a second potential that has an opposite polarity than the first (i.e. either negative or positive), such that a circuit is formed between the two terminals during operation of electrosurgical instruments connected thereto. Moreover, the functions of each terminal 311, 312 are interchangeable, i.e. their polarities can be switched as needed. In this case, each terminal 311, 312 is configured as a switch between bipolar ports 315 and 317 (BP1) and bipolar ports 316 and 318 (BP2), respectively. In other words, source terminal 311 switches between a source port 315 associated with bipolar instrument 301A and source port 316 associated with bipolar instrument 301B. Similarly, return terminal 312 switches between a return port 317 associated with bipolar instrument 301A, and return port 318 associated with bipolar instrument 301B. Bipolar instruments 301A, 301B are operable, for example, by a surgeon either directly or via a remote interface, to perform electrosurgical procedures on material 330, such as tissue for example. (Thus, "material 330" may also be referred to as "tissue 330" herein.) Tissue 330 can be any type of tissue, such as neural tissue, muscle tissue, vascular tissue, etc.

In operation, with reference to FIG. 3A, source terminal 311 and return terminal 312 are set to a first bipolar mode of operation, i.e. terminals 311, 312 are respectively electrically coupled to BP1 ports 315 and 317 to which bipolar instrument 301A is electrically coupled through wires 306A, 306B respectively. Thus, electrical flux energy flows from port 315, through wire 306A, and to a first, active electrode 303A of an end effector of electrosurgical instrument 301A in a direction depicted by arrow 320. Bipolar electrosurgical instrument 301A may be, for instance, a vessel sealer, forceps, or any instrument that has an end effector comprising two electrodes 303A, 304A. Consequently, any excess or residual electrical flux energy flows through a return electrode 304A of electrosurgical instrument 301A and return wire 306B along a direction indicated by arrow 321, to return port 317 and back to return terminal 312. Although only ports 315, 317 (i.e. BP1) are connected to source terminal 311 and return terminal 312, this is merely a convenient depiction intended to convey the first bipolar mode of operation, and other switching mechanisms that enable simultaneous use of instruments 301A-301B will be appreciated by those having ordinary skill in the art in light of this disclosure.

With reference now to FIG. 3B, source and return terminals 311, 312 are set to a second bipolar mode of operation. In this second bipolar mode of operation, terminals 311, 312 are respectively connected to BP2 ports 316 and 318 to which bipolar instrument 301B is electrically coupled. Thus, electrical flux energy flows from port 316, through wire 307A, and to an active electrode 303B of electrosurgical instrument 301B in a direction depicted by arrow 322. Electrosurgical instrument 301B may comprise any bipolar instrument, for instance, a vessel sealer, forceps, or any instrument that has an end effector comprising two electrodes 303B, 304B. Consequently, any excess flux energy that is not absorbed by tissue 330 or converted into another form (such as, for example, heat) flows through a return electrode 304B of electrosurgical instrument 301B, return wire 307B along a direction indicated by arrow 323, through return port 318, and back to return terminal 312. Although only ports 316, 318 of BP2 are connected to source terminal 311 and return terminal 312, this is merely a convenient depiction intended to convey the second bipolar mode of operation, and other switching mechanisms that enable simultaneous use of instruments 301A, 301B may be envisioned by those having ordinary skill in the art in light of the present disclosure.

With reference now to FIG. 3C, ESU 302 is configured to deliver electrical flux energy such that electrosurgical instrument 301B can be used as a monopolar instrument to apply the electrical flux energy via an active electrode 303B, while return electrode 304B of electrosurgical instrument 301B is disabled, i.e. electrically decoupled from any energy source or return. Electrosurgical instrument 301A can be used as an electrical flux energy return using one of its electrodes 304A as a return electrode. To achieve this, source terminal 311 is connected to BP2 port 316, while return terminal 312 is connected to BP1 port 317. To perform the function of a return electrode for monopolar operation of bipolar instrument 301B, at least the return electrode 304A of bipolar instrument 301A can be maintained in contact with the tissue 330, for example by a surgeon maintaining a position of the electrode in contact with the tissue. Thus, electrical flux energy flows from port 316, through wire 307A, and to the active electrode 303B of electrosurgical instrument 301B in a direction depicted by arrow 322. While electrosurgical instrument 301B is being used as a monopolar instrument, for example to spray or fulgurate tissue 330, excess flux energy can flow through tissue 330 along a direction indicated by arrow 324, through return electrode 304A of electrosurgical instrument 301A, through return wire 306B along a direction indicated by arrow 321, through return port 317, and back to return terminal 312.

In this embodiment, bipolar instrument 301B may be configured to function as a monopolar instrument for performing, for example, spray or fulgurate procedures on a section of tissue 330. This configuration may include configuring one of the two electrodes of the end effector of bipolar instrument 301B, such as electrode 303B, as an active electrode for monopolar operation, and ensuring that said active electrode and other components of instrument 301B are able to sustain the higher energy levels associated with monopolar energization and operation versus bipolar energization and operation. Consequently, ESU 302 can be configured to supply any additional energy that may be required for such monopolar operation. Further, any one of instruments 301A and 301B can be configured to act as the energy return, while the other instrument is configured to act as a monopolar instrument as described above. Moreover, two monopolar instruments may be set up with one of the monopolar instruments acting as an energy return by, for instance, switching the single electrode of the second monopolar instrument from a source port to a return port.

As described above with reference to the exemplary embodiment of FIG. 2, the surgeon operating instruments 301A-301B is able to exercise full control over the location and motion of the return electrode of bipolar instrument 301A, thereby being able to provide traction and counter traction on tissue 330 using both instruments simultaneously. As the distance between active electrode 303B of the end effector of electrosurgical instrument 301B and the return electrode 304A of the end effector of bipolar instrument 301A is smaller than a distance of the prior art methods using a return pad attached elsewhere on tissue 330, less energy is required to perform the same monopolar procedure using bipolar instrument 301B than traditional monopolar operation.

Figure 4:
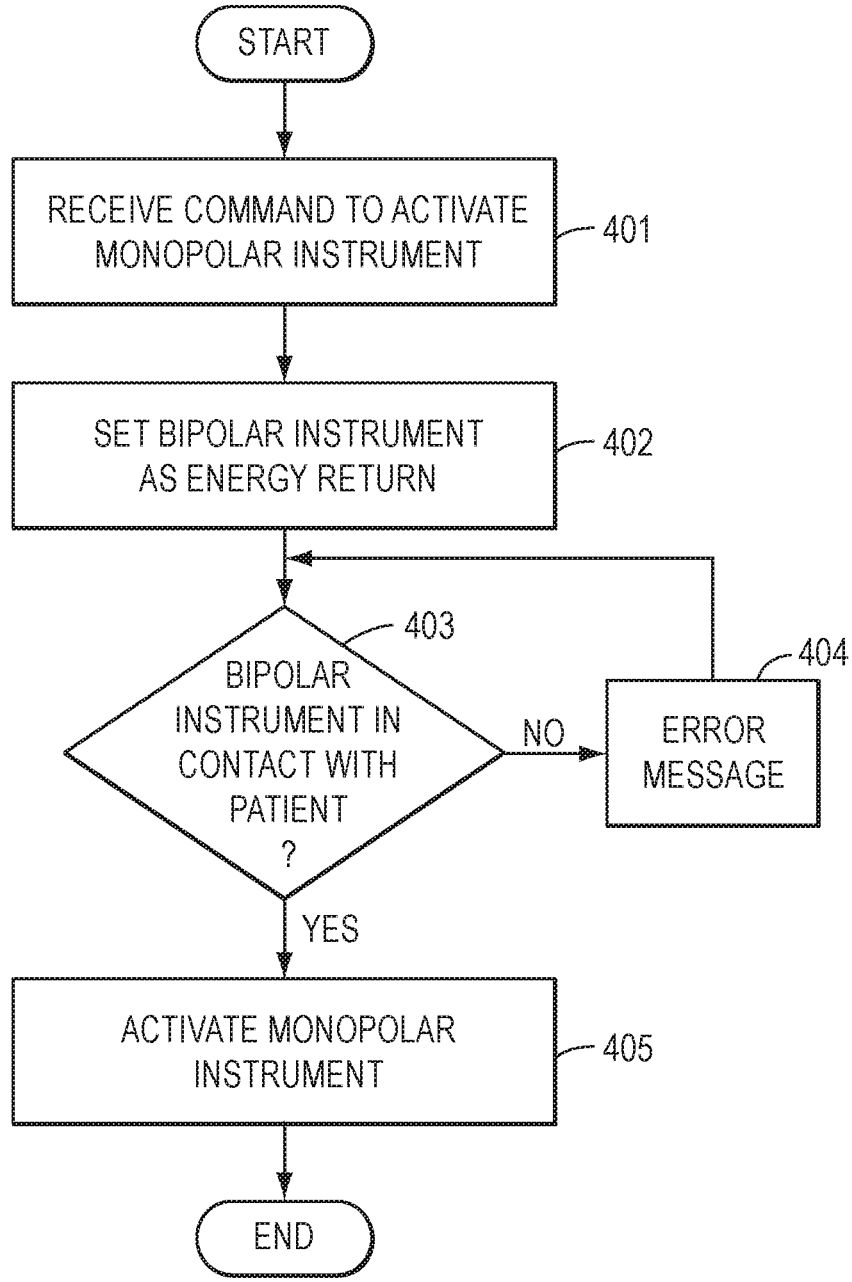
FIG. 4 depicts an exemplary workflow for using a bipolar electrosurgical instrument as an electrical energy return.

FIG. 4 depicts an exemplary method for using a bipolar electrosurgical instrument as an energy return. The method of FIG. 4 comprises operations that may be performed by one or more of a computer (such as computer system 151), ESUs (such as 102A-102B, 203, 302), or manipulator 152 as described in FIG. 1, alone or in any combination. Alternatively, the method of FIG. 4 may be performed by any appropriate component of the system on which it is implemented, as will be evident to persons having ordinary skill in the art in light of this disclosure. Moreover, the method of FIG. 4 can be performed using electrosurgical instruments in a teleoperated surgical system, or using electrosurgical instruments in a manual laparoscopic minimally-invasive system.

At 401, a command to activate a monopolar instrument is received from a surgeon. The command may be received from a master control console 150, or any other device in communication with an ESU, such as an interface coupled to the ESU that may be part of the instrument itself; alternatively the command may come from interaction directly with a GUI of the ESU. In response to the command, at 402, a bipolar instrument electrically coupled with the ESU is configured as an energy return. For example, an electrode of the bipolar instrument is switched to being placed in electrical communication with an energy return terminal of the ESU. Alternatively or in addition, an active electrode of the bipolar instrument is deactivated, such that the bipolar instrument is functioning solely as an energy return.

At 403, a determination is made whether or not the return electrode of the bipolar instrument is in contact with a patient (or any other type of living tissue). For instance, a small "trickle" current may be transmitted through the return electrode to determine whether or not the return electrode is in contact with the body. In some embodiments, the trickle current may be transmitted through a second instrument that is intended to be used as the monopolar instrument. Upon both the second (monopolar) instrument and the return electrode of the bipolar instrument being in physical contact with the tissue, the trickle current may be sensed by a sensor. A trickle current may comprise, for instance, a small amount of current that is sufficiently large to sense and sufficiently small, such that it has no effect on the tissue, and can vary depending on the surface area of the electrode(s). If the trickle current is not sensed, the method optionally provides error feedback at 404 via, for example, a message or other visual indicator, audible feedback, tactile feedback, etc., and returns to 403 to continue to monitor the return electrode of the bipolar instrument. If the current is sensed, then the method proceeds to activate the monopolar instrument at 405. Sensing step 403 is used because if the return electrode is not properly contacted with the tissue, the energy transmitted through the monopolar may be ungrounded, or may find a return path elsewhere on the patient's body, resulting in a suboptimal procedure.

If the current is sensed at 403, then the monopolar instrument is activated at 405. This activation can occur by electrically coupling and delivering electrical current to the single active electrode of the monopolar instrument to a source terminal of an ESU, as described in FIG. 2B. Alternatively or in addition, as described above, this activation can occur by electrically coupling and delivering electrical current to one electrode of a bipolar instrument, as described in FIG. 3A. Consequently, during operation of the monopolar instrument, the flux energy flows through the monopolar instrument and the tissue, and is returned via the return electrode of the bipolar instrument (that is now operating as an energy return).

Although the operations of FIG. 4 are depicted and presented above in an order, alternative ordering may be contemplated by those having ordinary skill in the art in light of this disclosure. For instance, setting the bipolar instrument as an energy return at 402 may be performed subsequent to determining the contact with the tissue at 403. Alternatively or in addition, step 402 may be unnecessary in the case that the bipolar instrument is already operational, since only the return electrode must maintain contact with the patient for the bipolar instrument to function as an energy return. Further, upon sensing that the return electrode is not in contact with the patient, the electrical coupling of the single active electrode may be disconnected, or the active electrode set to a neutral potential, thus stopping the electrical energy flux. The electrical energy flux may be resumed upon sensing that the return electrode is in contact with the patient.

In some embodiments, a distance between the active and return electrodes of the two electrosurgical instruments may be determined based on, for instance, an amount of resistance subjected to an electrical energy flow between the two electrodes. The energy flow may be the operational electrical flux associated with the electrosurgical procedure, or a trickle current as described above. In either case, the resistance is proportional to the distance, and can be used to determine how much energy needs to be applied to effectuate the electrosurgical procedure being performed. For instance, the farther away the return electrode is from the active electrode of the electrosurgical instrument performing the procedure (a monopolar electrosurgical instrument or a bipolar electrosurgical instrument being used in a monopolar mode), the more energy is required for the monopolar-configured electrode of the electrosurgical instrument to perform its intended function. Sensors for detecting resistance and energy flow between the electrodes of the two instruments (for instance of an electrical flux or trickle current) may be positioned within one or both surgical instruments, or within an ESU or other component of an electrosurgical system. Any voltage or current sensor may be used. In other embodiments, the resistance and/or an energy-level recommendation may be output in real-time via an interface, enabling a user, e.g., the surgeon, to determine whether to manually adjust the output energy (i.e. voltage) of the electrode serving as the monopolar delivery electrode while performing the procedure.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

Exemplary embodiments, including the various operational methods described herein, can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to affect the various responses and signal processing in accordance with various exemplary embodiments of the present disclosure, such as a console for operating various modes of an ESU, can be implemented by a processor of or in conjunction with the control cart and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

The nature of information depicted in the figures and described herein is exemplary. Those persons having skilled in the art would appreciate modifications to the displays can be made, such as, for example, depending on the number and type of controls desired, the number and/or type of instruments to be used, and/or the functions of the instruments used and the type of electrical energy fluxes supplied by electrical energy flux supply units. The various instrument setups depicted in the drawings and described herein are exemplary in nature and the present disclosure contemplates other instrument setups.

This description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Further, the terms "immediate" and "real-time" may mean a response that occurs within a time period of no more than a few seconds. In exemplary embodiments, real-time responses from ESUs described herein may be provided to a user interface within 1-2 seconds.

It is to be understood that the particular examples and embodiments set forth herein are nonlimiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. An electrosurgical flux supply unit, comprising:
    first and second terminals configured to be electrically coupled with first and second electrodes, respectively, of a first end effector of a first bipolar electrosurgical instrument operably coupled to the electrosurgical flux supply unit;
    third and fourth terminals configured to be electrically coupled with third and fourth electrodes, respectively, of a second end effector of a second bipolar electrosurgical instrument operably coupled to the electrosurgical flux supply unit;
    an electrosurgical flux source terminal;
    an electrosurgical flux return terminal; and
    an electrical switching mechanism selectively configurable between a first state and a second state, wherein:

in the first state, the electrosurgical flux source terminal is electrically coupled with the first terminal and the electrosurgical flux return terminal is electrically coupled with the second terminal, and in the second state, the electrosurgical flux source terminal is electrically coupled with the third terminal and the electrosurgical flux return terminal is electrically coupled with the second terminal, wherein the electrosurgical flux supply unit is configured to:

in the first state, supply bipolar electrosurgical flux to flow between the electrosurgical flux source terminal and the electrosurgical flux return terminal; and in the second state, supply monopolar electrosurgical flux to flow between the electrosurgical flux source terminal and the electrosurgical flux return terminal.

2. The electrosurgical flux supply unit of claim 1, wherein, in the second state, the electrosurgical flux supply unit is configured to flow at least a portion of the supplied monopolar electrosurgical flux from the third terminal to the third electrode, from the third electrode to the second electrode, and from the second electrode to the second terminal.

3. The electrosurgical flux supply unit of claim 1, wherein the electrosurgical flux supply unit is configured to, in the second state:

prior to the supply of monopolar electrosurgical flux, supply electrical energy configured to generate a trickle current between the third terminal and the second terminal, and condition the supply of the monopolar electrosurgical flux between the third terminal and the second terminal based on whether the trickle current is able to flow between the third terminal and the second terminal.

4. A system for electrosurgical energy delivery, the system comprising:

an electrosurgical flux supply unit;

a first electrosurgical instrument electrically coupled to the electrosurgical flux supply unit, the first electrosurgical instrument comprising a first shaft and a first end effector coupled to the first shaft, the first end effector comprising a first electrode and a second electrode; and a second electrosurgical instrument electrically coupled to the electrosurgical flux supply unit, the second electrosurgical instrument comprising a second shaft and a second end effector coupled to the second shaft, the second end effector comprising a third electrode;

wherein the electrosurgical flux supply unit is configured to:

in a first state, supply bipolar electrosurgical flux to flow between the first electrode and the second electrode, and in a second state, supply monopolar electrosurgical flux to flow between the third electrode and the second electrode.

5. The system of claim 4, wherein the third electrode is configured to perform one or more of a spray procedure, a blend procedure, or a fulguration procedure.

6. The system of claim 4, wherein the second electrode has a surface area that is relatively larger than a surface area of the third electrode.

7. The system of claim 4, further comprising a sensor configured to sense a resistance between the third electrode of the second electrosurgical instrument and the second electrode of the first electrosurgical instrument based in part on sensing the monopolar electrosurgical flux flowing between the third electrode and the second electrode.

8. The system of claim 7, wherein the electrosurgical flux supply unit is further configured to adjust a voltage of the supplied monopolar electrosurgical flux based on the resistance sensed by the sensor.

9. The system of claim 7, further comprising a feedback mechanism configured to output feedback prompting a user to adjust a voltage of the supplied monopolar electrosurgical flux based on the resistance.

10. The system of claim 4, wherein:

the first electrosurgical instrument is a bipolar surgical instrument; and the second electrosurgical instrument is a monopolar surgical instrument.

11. The system of claim 4, wherein:

the first electrosurgical instrument is a first bipolar surgical instrument; and the second electrosurgical instrument is a second bipolar surgical instrument.

12. The system of claim 4, wherein the electrosurgical flux supply unit is configured to, in the second state:

prior to supply of the monopolar electrosurgical flux, supply electrical energy configured to generate a trickle current between the third electrode and the second electrode, and condition the supply of the monopolar electrosurgical flux between the third electrode and the second electrode based on whether the trickle current is able to flow between the third electrode and the second electrode.

13. A method, comprising:

setting a first electrode of a first end effector of a monopolar electrosurgical instrument at a first electrical potential;

setting a second electrode of a pair of electrodes of a second end effector of a bipolar electrosurgical instrument at a second electrical potential, the second electrical potential being set at a relative ground to the first electrical potential; and supplying a monopolar electrosurgical flux to flow between the first electrode and the second electrode.

14. The method of claim 13, further comprising sensing for a current flowing between the second electrode and the first electrode.

15. The method of claim 14, further comprising:

positioning the first end effector and the second end effector relative to a material; and determining if the second electrode is in contact with the material based on whether a current is sensed flowing between the first electrode and the second electrode.

16. The method of claim 15, further comprising generating error feedback on condition of determining that the second electrode is not in contact with the material.

17. The method of claim 15, further comprising setting the first electrode at a neutral electrical potential on condition of determining that the second electrode is not in contact with the material.

18. The method of claim 14, further comprising, on condition of sensing a current flowing between the first electrode and the second electrode, determining a distance between the first electrode and the second electrode based on a magnitude of the sensed current.

19. The method of claim 14, further comprising, on condition of sensing a current flowing between the first electrode and the second electrode, adjusting an amount of the monopolar electrosurgical flux supplied based on a magnitude of the sensed current.

20. The method of claim 14, further comprising, on condition of sensing a current flowing between the first electrode and the second electrode, outputting feedback to indicate to a user to adjust at least one of the first and second electrical potentials based on a magnitude of the sensed current.

* * * * *